United States Patent
Aittokoski (10) Patent No.: US 12,364,407 B2
(45) Date of Patent: *Jul. 22, 2025

(54) HEART RATE MONITORING DEVICE, SYSTEM, AND METHOD FOR INCREASING PERFORMANCE IMPROVEMENT EFFICIENCY

(71) Applicant: EMFIT OY, Vaajakoski (FI)

(72) Inventor: Timo Aittokoski, Vaajakoski (FI)

(73) Assignee: EMFIT OY, Vaajakoski (FI)

( * ) Notice: Subject to any disclaimer, the term of this patent is extended or adjusted under 35 U.S.C. 154(b) by 576 days.

This patent is subject to a terminal disclaimer.

(21) Appl. No.: 17/328,948

(22) Filed: May 24, 2021

(65) Prior Publication Data

US 2021/0290082 A1 Sep. 23, 2021

Related U.S. Application Data

(63) Continuation of application No. 15/761,809, filed as application No. PCT/US2016/053343 on Sep. 23, 2016, now Pat. No. 11,013,424.

(60) Provisional application No. 62/274,951, filed on Jan. 5, 2016, provisional application No. 62/222,692, filed on Sep. 23, 2015.

(51) Int. Cl.
*A61B 5/0255* (2006.01)
*A61B 5/00* (2006.01)
(Continued)

(52) U.S. Cl.
CPC .......... *A61B 5/0255* (2013.01); *A61B 5/0002* (2013.01); *A61B 5/1102* (2013.01);
(Continued)

(58) Field of Classification Search
CPC .......................... A61B 5/0255; A61B 5/0002
(Continued)

(56) References Cited

U.S. PATENT DOCUMENTS 4,625,733 A 12/1986 Saynajakangas
5,486,818 A 1/1996 Loponen
(Continued)

FOREIGN PATENT DOCUMENTS

| CA | 2825405 A1 * | 8/2012 | ........... A61B 5/0002 |
| WO | WO-2009138976 A2 * | 11/2009 | ........... A61B 5/0002 |
| WO | WO-2013111785 A1 * | 8/2013 | ........... A61B 5/0002 |

OTHER PUBLICATIONS

Selected printout of electrodes, monitors,& sensors from sleeppreviewmag.com, believed to have been published on ore before Dec. 31, 2016.

(Continued)

*Primary Examiner* — Nicole F Johnson
(74) *Attorney, Agent, or Firm* — Hassan Abbas Shakir; Shakir Law PLLC (57) ABSTRACT

A heart-rate monitoring system for a monitoring subject for increasing a performance improvement efficiency by the monitoring subject includes a heart-rate monitoring device having a sensor. The sensor is not in direct physical contact with the monitoring subject. The sensor provides sensing data; the heart-rate monitoring device calculates, from the sensing data, monitoring data relative to heart rate variability of the monitoring subject. The system includes an application server processing the monitoring data to calculate processed data and a user device for displaying the processed data in a format that increases the performance improvement efficiency by the monitoring subject.

13 Claims, 5 Drawing Sheets

(51) Int. Cl.
*A61B 5/11* (2006.01)
*A61B 5/024* (2006.01)

(52) U.S. Cl.
CPC ........ *A61B 5/6891* (2013.01); *A61B 5/02405* (2013.01); *A61B 5/6892* (2013.01)

(58) Field of Classification Search
USPC .......................................................... 600/508
See application file for complete search history.

(56) References Cited

U.S. PATENT DOCUMENTS

| | | | |
|---|---|---|---|
| 5,611,346 | A | 3/1997 | Heikkila et al. |
| 5,628,324 | A | 5/1997 | Sarbach |
| 5,690,119 | A | 11/1997 | Rytky et al. |
| 5,719,825 | A | 2/1998 | Dotter |
| 6,104,947 | A | 8/2000 | Heikkila et al. |
| 6,277,080 | B1 | 8/2001 | Nissilä et al. |
| 6,361,502 | B1 | 3/2002 | Puolakanaho et al. |
| 6,405,077 | B1 | 6/2002 | Birnbaum et al. |
| 6,418,394 | B1 | 7/2002 | Puolakanaho et al. |
| 6,477,397 | B1 | 11/2002 | Ronkainen et al. |
| 6,537,227 | B2 | 3/2003 | Kinnunen et al. |
| 6,666,562 | B2 | 12/2003 | Nissilä |
| 6,714,812 | B1 | 3/2004 | Karjalainen et al. |
| D492,784 | S | 7/2004 | Lax |
| D492,999 | S | 7/2004 | Lax |
| 6,916,979 | B2 | 7/2005 | Raisanen |
| 6,996,891 | B1 | 2/2006 | Raisanen |
| 7,216,417 | B2 | 5/2007 | Raisanen |
| 7,808,395 | B2 | 10/2010 | Raisanen |
| 7,954,385 | B2 | 6/2011 | Raisanen |
| 2007/0299325 | A1* | 12/2007 | Farrell ................. A61B 5/0002 600/301 |
| 2011/0004072 | A1 | 1/2011 | Fletcher et al. |
| 2011/0046498 | A1 | 2/2011 | Klap |
| 2012/0123279 | A1 | 5/2012 | Brueser et al. |
| 2012/0238800 | A1 | 9/2012 | Naujokat |
| 2012/0330109 | A1 | 12/2012 | Tran |
| 2013/0173302 | A1 | 7/2013 | Hyde et al. |
| 2013/0237776 | A1 | 9/2013 | Ong et al. |
| 2013/0267791 | A1* | 10/2013 | Halperin .............. A61B 5/6891 600/300 |

OTHER PUBLICATIONS

Article "Firstbeat Bodyguard 2 Guide" authored by Firstbeat Technologies Oy, retrieved Dec. 9, 2019 from www.firstbeat.com/wp-content/uploads/2015/10/150811_Bodyguard2_Guide_ENG.pdf, believed to have been published on or before Dec. 31, 2015.

Article "HRV Standard" authored by Kubios Oy, retrieved Dec. 9, 2019 from www.kubios.com/downloads/Kubios-HRV-Standard.pdf, believed to have been published on or before Dec. 31, 2014.

"RS800CX User Manual", authored by Polar Electro Oy, believed to have been published on or before Aug. 31, 2013.

"Polar RS800sd A complete training system for runners and endurance athletes", authored by Polar Electro Oy, believed to have been published on or before Aug. 31, 2013.

Doctoral Thesis "Sleep Assessment Using Bed-Mounted Sensors", authored by Daniel Waltisberg, Published by ETH Zurich, Switzerland, believed to have been published on or before Dec. 31, 2017.

"Unobtrusive Online Monitoring of Sleep at Home", authored by Joonas Paalasmaa, presented 34th Annual International Conference of the IEEE EMBS San Diego, California USA, Aug. 28-Sep. 1, 2012.

"The Actiheart User Manual" issue ersion 4.0.35, Dated Jan. 7, 2010, 95 pgs.

International Search Report in patent application PCT/US2020/026037 issued Jun. 25, 2020 by the Russian Federal Institute of Industrial Property, in English.

Written Opinion of the International Searching Authority in patent application PCT/US2020/026037 issued Jun. 25, 2020 by the Russian Federal Institute of Industrial Property, in English.

International Search Report in patent application PCT/US2016/053343 issued Jan. 12, 2017 by the Russian Federal Institute of Industrial Property, in English.

Written Opinion of the International Searching Authority in patent application PCT/US2016/053343 issued Jan. 12, 2017 by the Russian Federal Institute of Industrial Property, in English.

Article "Accuracy of the Suunto system for heart rate variability analysis during a tilt-test" authored by Anthony Bouillod et al, published Revista Brasileira Cineantropometria e Desempenho Humano, published 2015, edition 17(4), pp. 409-417.

Article "Ballistocardiogram Signal Processing: A Literature Review" authored by Ibrahim Sadek, published Jul. 3, 2018 on arxiv.org/abs/1807.00951.

Article "Contact-Free Piezo Electric Sensor used for Real-Time Analysis of Inter Beat Interval Series" authored by Yaniv Katz et al., published 2016 in Computing in Cardiology 2016; vol. 43.

Article "Effects of sensor type and sensor location on signal quality in bed mounted ballistocardiographic heart rate and respiration monitoring", authored by Antti Vehkaoja et al., published 2015, retrieved from tutcris.tut.fi/portal/files/3924267/Effects_of_Sensor_Type_and_Sensor_Location_on_Signal_Quality_in_Bed_Mounted_Ballistocardiographic_Heart_Rate_and_Respiration_Monitoring.pdf.

* cited by examiner

HEART RATE MONITORING DEVICE, SYSTEM, AND METHOD FOR INCREASING PERFORMANCE IMPROVEMENT EFFICIENCY

CROSS-REFERENCE TO RELATED APPLICATIONS

This application is a continuation of and claims priority from U.S. Ser. No. 15/761,809 filed Mar. 20, 2018, which is currently pending and which is hereby incorporated by reference in its entirety for all purposes.

U.S. Ser. No. 15/761,809 is a National Stage Entry of and claims priority from PCT/US2016/053343 filed Sep. 23, 2016, which is expired and which is hereby incorporated by reference in its entirety for all purposes.

Application PCT/US2016/053343 claims priority from Provisional Application 62/274,951 filed Jan. 5, 2016, which is hereby incorporated by reference in its entirety for all purposes.

Application PCT/US2016/053343 claims priority from Provisional Application 62/222,692 filed Sep. 23, 2015, which is hereby incorporated by reference in its entirety for all purposes.

BACKGROUND OF THE INVENTION

1. Field of the Invention

The invention is directed to heart-rate monitoring of a monitoring subject to and providing user-accessible feedback for increasing performance improvement efficiency by the monitoring subject.

2. Discussion of the Related Art

Everyone must sleep, but the reasons why are not fully know. What is well understood is that sleep is one of the most essential physical states for an individual (i.e., user) to recover from exertion and stress.

To fully recover physically, mentally, or both, individuals interested in their performance, whether an athlete, business leader, artist, military personnel, pilots, et al. should have sufficient amount of sleep, with sufficiently high quality, so that sleep can constitute solid base for efficient recovery, i.e., performance improvement efficiency, that is increase the speed, degree, and way by which the individual improves their performance. Thus, measuring and understanding progress, magnitude and efficiency of recovery during a night's sleep, when most of recovery occurs, is fundamental.

In the scientific literature, heart rate variability ("HRV") has been considered as a method to offer views into the physiology of a human (or animal) body, and to monitor recovery status by measuring and analyzing carefully individual heart beats.

Even though it is widely believed by those not trained in physiology that a human heart beats regularly, like a metronome, this is not the scientific case. Instead, even if heart rate is steady, for example, at 60 beats per minute, time intervals from beat-to-beat will vary considerably. Peaks in ballistocardiogram or electrocardiogram may occur, for example, at beat-to-beat intervals ("BBI") of 890 ms, 1020 ms, 980 ms, 1005 ms, etc., i.e., HRV, having an average of 1000 ms in some time window, corresponding to 60 beats per minute.

Somewhat surprisingly, the greater the irregularity of the BBI of a heart i.e., the heart rate variability (HRV) is higher, the more fit and healthy the individual is. In contrast, a reduction in heart rate variability may indicate many health or lifestyle related problems. Furthermore, certain HRV-based parameters tell us about the state of the autonomic nervous system, giving us valuable view into what is happening inside our body.

In long term monitoring of HRV, a user can determine whether his/her cardiovascular fitness is increasing, as baseline HRV increases along with it. In short term, HRV gives valuable information about stress and recovery. Both stress and recovery tend to decrease HRV from the baseline, which is when a user should avoid heavy exercise sessions until HRV has returned to baseline values.

There are several different methods, or indices, to quantify HRV numerically, but are usually methods are categorized in to three different classes:

1. Time-domain methods, which are based on direct statistics of beat-to-beat intervals. These are for example:
    SDNN, the standard deviation of beat-to-beat intervals;
    RMSSD ("root mean square of successive differences"), the square root of the mean of the squares of the successive differences between adjacent beat-to-beat intervals;
    SDSD ("standard deviation of successive differences"), the standard deviation of the successive differences between adjacent beat-to-beat intervals;
    NN50, the number of pairs of successive beat-to-beat intervals that differ by more than 50 ms;
    pNN50, the proportion of NN50 divided by total number of beat-to-beat intervals;
    NN20, the number of pairs of successive beat-to-beat intervals that differ by more than 20 ms; and
    pNN20, the proportion of NN20 divided by total number of beat-to-beat intervals.
2. Frequency-domain methods, where beat-to-beat intervals are assigned in to certain frequency bands using for example Fourier transform. Typically the bands are defined as high frequency (HF) from 0.15 to 0.4 Hz, low frequency (LF) from 0.04 to 0.15 Hz, and the very low frequency (VLF) from 0.0033 to 0.04 Hz. One usual method is to compute and compare power of each band.
3. Geometric methods
    Beat-to-beat intervals can be translated in to graphical presentation, to facilitate better understanding of HRV behavior. From graphical presentation it is possible to derive numerical measures. One of the most well-known geometric method is so called Poincare plot.

RMSSD is one of the most widely used time domain heart rate variability values. In the scientific literature RMSSD is widely accepted as a measure of parasympathetic nervous system (PNS) activity. According to Wikipedia, PNS is responsible for stimulation of "rest-and-digest" or "feed and breed" activities that occur when the body is at rest, and complementary to that of the sympathetic nervous system (SNS), which is responsible for stimulating activities associated with the fight-or-flight response.

For efficient recovery from training and stress, it is essential that parasympathetic nervous system is active, and our body gets sufficient rest and replenishment. With HRV RMSSD value one can monitor what his/her general baseline value is and see how heavy exercise, stress, etc. factors influence it, and see when the value gets back to baseline, indicating for example capability to take another bout of heavy exercise. RMSSD can be measured in different length time windows and in different positions, e.g. supine, sitting or standing. It is preferable to measure RMSSD in situation where both heart and respiration rates are even and slow, and there is no excessive movement.

Currently there are some applications that use heart rate variability (HRV) and its different measures, most often RMSSD as indicator of the status of the body. Individual heart beat intervals can be acquired most reliably using electrocardiogram (ECG), but due to its complexity and expensive equipment, this approach is limited to hospitals, laboratories, research facilities, etc. For professional consumer level Firstbeat offers BodyGuard system, which uses two ECG electrodes, and can be worn up to 72 hours. BodyGuard data is meant to be analyzed as a service provided by Firstbeat, although the heart beat intervals can be exported for third party analysis. Further, Actiheart by CamNtech as a device is very similar to Firstbeat, utilizing two ECG electrodes, but it is apparently aimed more in to clinical practice and research.

At a consumer level, probably the most common way to acquire heart beat intervals is by the use of wrist heart rate monitor and chest strap sensor combination. There are several manufacturers offering devices in this genre, i.e. Polar, Suunto, Garmin, etc. Downside of this approach is that the data must be exported and processed to HRV indices and graphs using some third party software, such as Kubios HRV, making the whole process cumbersome and laborious.

To ease the measurement process, there are some mobile app solutions, most notably BioForce HRV and Ithlete. They both use chest strap to acquire heart beat intervals in the morning after waking up, using 3 minute and 1 minute measurement window, respectively, and as a result they produce single number (log transformed RMSSD multiplied by 20) varying from 0 to 100, and indicating how fit the person is for the day.

As can be seen, currently there is no easy nor automated way of measuring HRV data, but it requires some degree of enthusiasm to wear either electrodes or chest strap, and analyze the data. Further, for whole night measurement, several people have reported that long term use of electrodes may irritate the skin, and wearing chestband feels annoying and may disturb sleep quality essentially.

Measurement of morning RMSSD is somewhat easier, although there is always burden to accomplish that task each and every morning. There is also problem in underlying assumption of measuring morning RMSSD in that it gives indication of recovery status, or indication on how fit you are for the new day. Problem with this assumption is that RMSSD is heavily fluctuating both in long and short term and for this reason value of "snapshot" HRV indices might be compromised.

Thus, what is desired is a device, system and method of HRV monitoring that overcomes the drawbacks in the known art, and that provides easily interpretable data to a user to increase their performance improvement efficiency.

SUMMARY OF THE INVENTION

These and other objectives are met by the inventive device, system and method of HRV monitoring that overcomes the drawbacks in the known art, and that provides easily interpretable data to a user to increase their performance improvement efficiency.

A heart-rate monitoring system for a monitoring subject for increasing a performance improvement efficiency by the monitoring subject includes a heart-rate monitoring device having a sensor. The sensor is not in direct physical contact with the monitoring subject. The sensor provides sensing data; the heart-rate monitoring device calculates, from the sensing data, monitoring data relative to heart rate variability of the monitoring subject. The system includes an application server processing the monitoring data to calculate processed data and a user device for displaying the processed data in a format that increases the performance improvement efficiency by the monitoring subject.

The heart-rate monitoring system includes a communication network that is partially wireless, wherein the application server, the heart-rate monitoring device, and the user device are in communication with each other.

A heart-rate monitoring method of increasing a performance improvement efficiency of a monitoring subject includes the steps of:
  (a) monitoring a heart-rate variability of the monitoring subject using a heart-rate monitoring device to obtain sensing data;
  (b) calculating, by a first processor, monitoring data from the sensing data;
  (c) calculating, by a second processor, processed data from the monitoring data;
  (d) presenting, to the monitoring subject, on a user device the processed data in a format that increases the performance improvement efficiency by the monitoring subject.

The monitoring data includes time measurements between heart beats of the monitoring subject, i.e., BBI.

DETAILED DESCRIPTION OF THE INVENTION

The following detailed description is of the best mode or modes of the invention presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention. In the various views of the drawings, like reference characters designate like or similar parts.

All technical and scientific terms shall have the same meaning as commonly understood by one of ordinary skill in the art. Nonetheless, the following terms are defined below to aid in the understanding of the disclosure and the definitions apply to all parts of speech of the term regardless whether the term is defined explicitly as such.

"About," "approximately," or "substantially similar" refer to a 10% variation from the nominal value. Even if not explicitly stated, it is to be understood that a variation is always included in a given value, whether or not the variation is specifically referenced.

Forms of the verb "to capture" mean to (a) acquire image data of an object through one or more sensors and (b) save the data to a file having any suitable format to any suitable memory storage.

"Computing device," or interchangeably "hardware," is intended in this disclosure for all purposes to be interpreted broadly and is defined for all uses, all devices, and/or all systems and/or systems in this disclosure as a device comprising at least a central processing unit, a communications device for interfacing with a data network, transitory computer-readable memory, and/or a non-transitory computer-readable memory and/or media. The central processing unit carries out the instructions of one or more computer programs stored in the non-transitory computer-readable memory and/or media by performing arithmetical, logical, and input/output operations to accomplish in whole or in part one or more steps of any method described herein.

A computing device is usable by one or more users, other computing devices directly and/or indirectly, actively and/or passively for one or more suitable functions herein. The computing device may be embodied as computer, a laptop, a tablet computer, a smartphone, and/or any other suitable device and may also be a networked computing device, a server, or the like. Where beneficial, a computing device preferably includes one or more human input devices such as a computer mouse and/or keyboard and one or more human interaction device such as one or more monitors. A computing device may refer to any input, output, and/or calculating device associated which provides for, supplements, realizes, accomplishes, enhances, and/or augments one or more functions, goals, and/or features associated with the present invention to one or more users.

Although one computing device may be shown and/or described, multiple computing devices may be used. Conversely, where multiple computing devices are shown and/or described, a single computing device may be used.

"Computer program," or interchangeably "software," means any set of instructions stored in a non-transitory computer-readable memory or non-transitory computer-readable media for executing one or more suitable functions and/or for executing one or more methods in this disclosure. Even if not explicitly mentioned, in this disclosure, a computing device includes software having any set of instructions stored in non-transitory computer-readable memory or non-transitory computer-readable media for executing one or more suitable functions and/or for executing one or more methods in this disclosure.

"Network" or "communication network" may mean one or more communications networks, such as the internet, Bluetooth, RS232, LAN, WAN, suitable for carrying out one or more portions and/or all features of the present invention and regardless of whether the network is wired or wireless of any form.

"Network interface" may mean any suitable device that provides access to a network by a member of the network. For example, a network interface to a Wi-Fi system may be a network router or modem. For example, in a Bluetooth network the communications device itself may be the network interface.

"Non-transitory computer-readable memory," or interchangeably "non-transitory computer-readable media," may be a hard drive, solid state drive, compact disk drive, DVD drive, and/or the like for storing the one or more computer programs.

"User" means one or more individuals, persons, and/or groups who may have a need, desire, or intent to one or more system and/or methods in this disclosure in whole or in part. A user of one or more features of this disclosure need not necessarily be the same user or a related user of one or more other features of this disclosure. Moreover, a user of one feature may not be aware of another user of the same or a different feature. Where one user is shown and/or described, multiple users may be present. Where multiple users are shown and/or described, a single user may be present. Although it is preferred for a variety of reasons that one user or one group of users execute the one or more steps described herein, this disclosure should not be considered limited without such a switch in the identity of the users being explicitly described. Thus, where one user or users is described as performing a step or a portion of a step, another user or users may perform a subsequent or previous step or a subsequent or previous portion of the step performed by the other user or users. It should be understood that were advantageous or desired one or more users may be authorized or pre-authorized to access one or more data or results derived from data and in order to prevent access by one or more other users. Such an authorization or pre-authorization may also be made sensitive to the data itself, wherein, for example, only some data is shared once a threshold has been reached. It should be understood that social media accounts by a user of one or more system and/or methods in this disclosure may be considered to be a user separate from the user who owns, uses, or operates the social media account.

Where appropriate, other terms and concepts are defined elsewhere in the disclosure. The omission of such definitions from this section shall not be construed that the terms and concepts have not been properly defined for any intended purpose.

Figure 1:
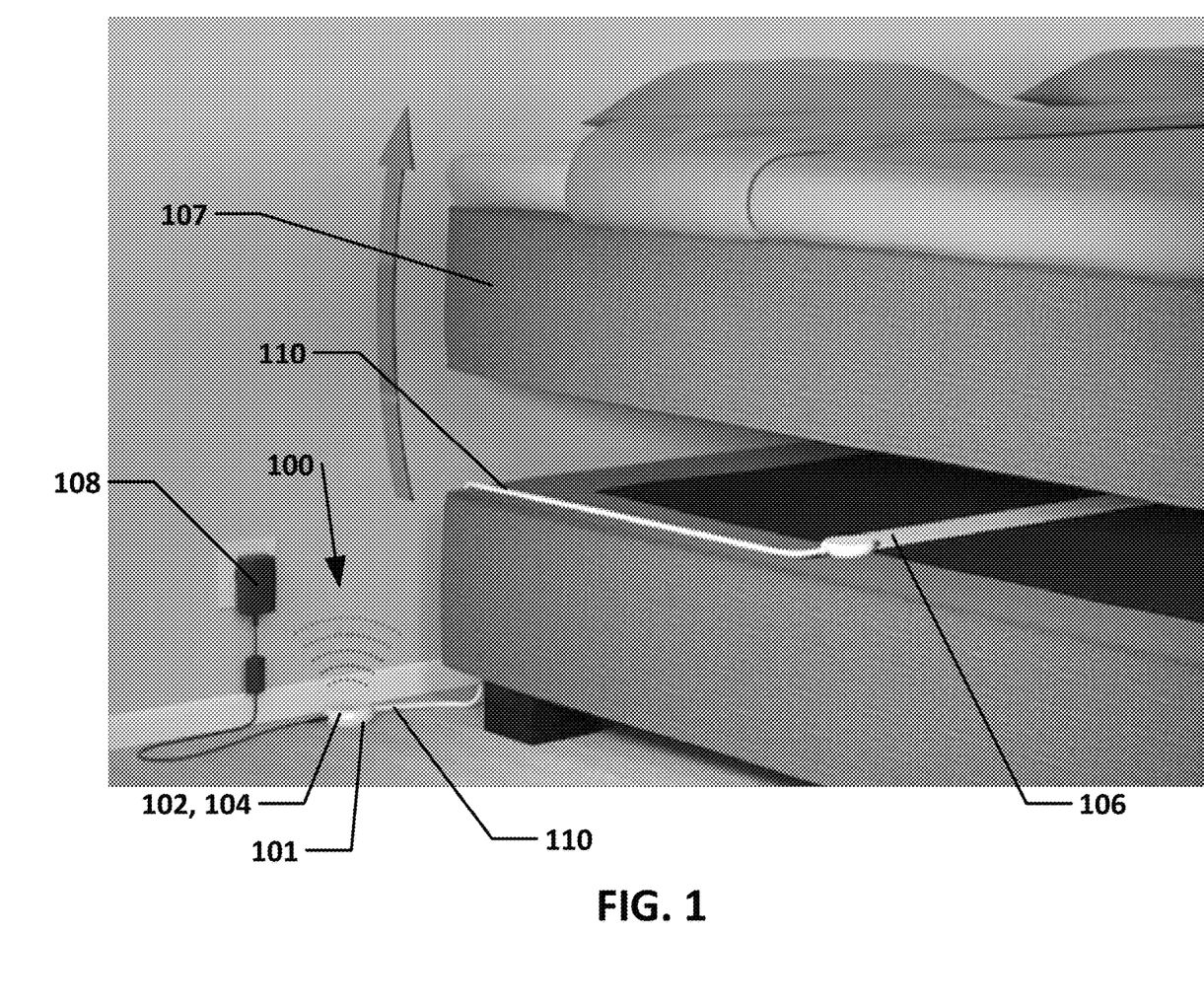
FIG. 1 is an illustrative view of a heart-rate monitoring device showing an under mattress installation in accordance with one or more embodiments of the present invention.

FIG. 1 is an illustrative view of a heart-rate monitoring device showing an under mattress installation in accordance with one or more embodiments of the present invention.

Figure 2:
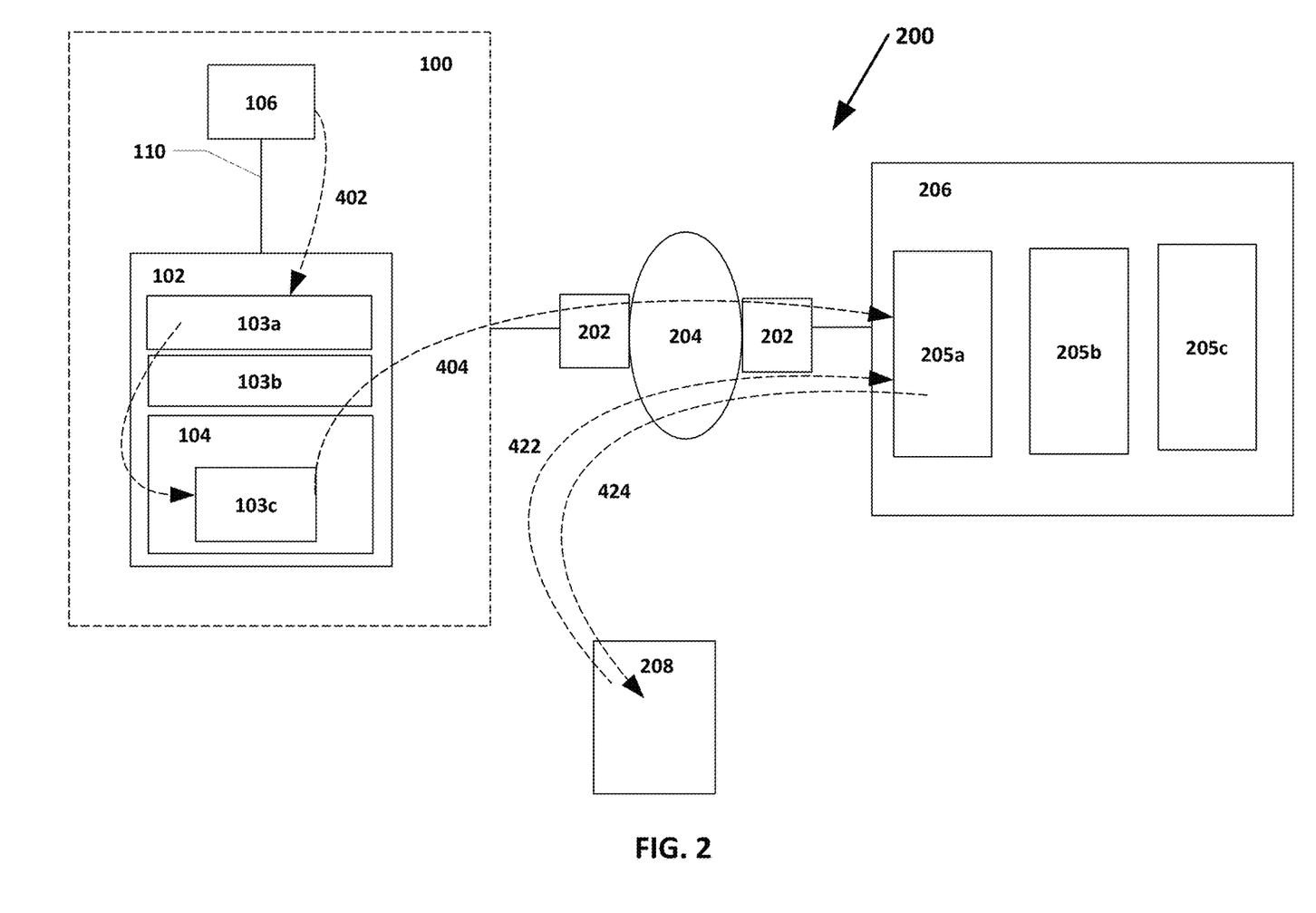
FIG. 2 is a schematic view of a heart-rate monitoring system in accordance with one or more embodiments of the present invention.

FIG. 2 is a schematic view of a heart-rate monitoring system in accordance with one or more embodiments of the present invention.

Figure 3:
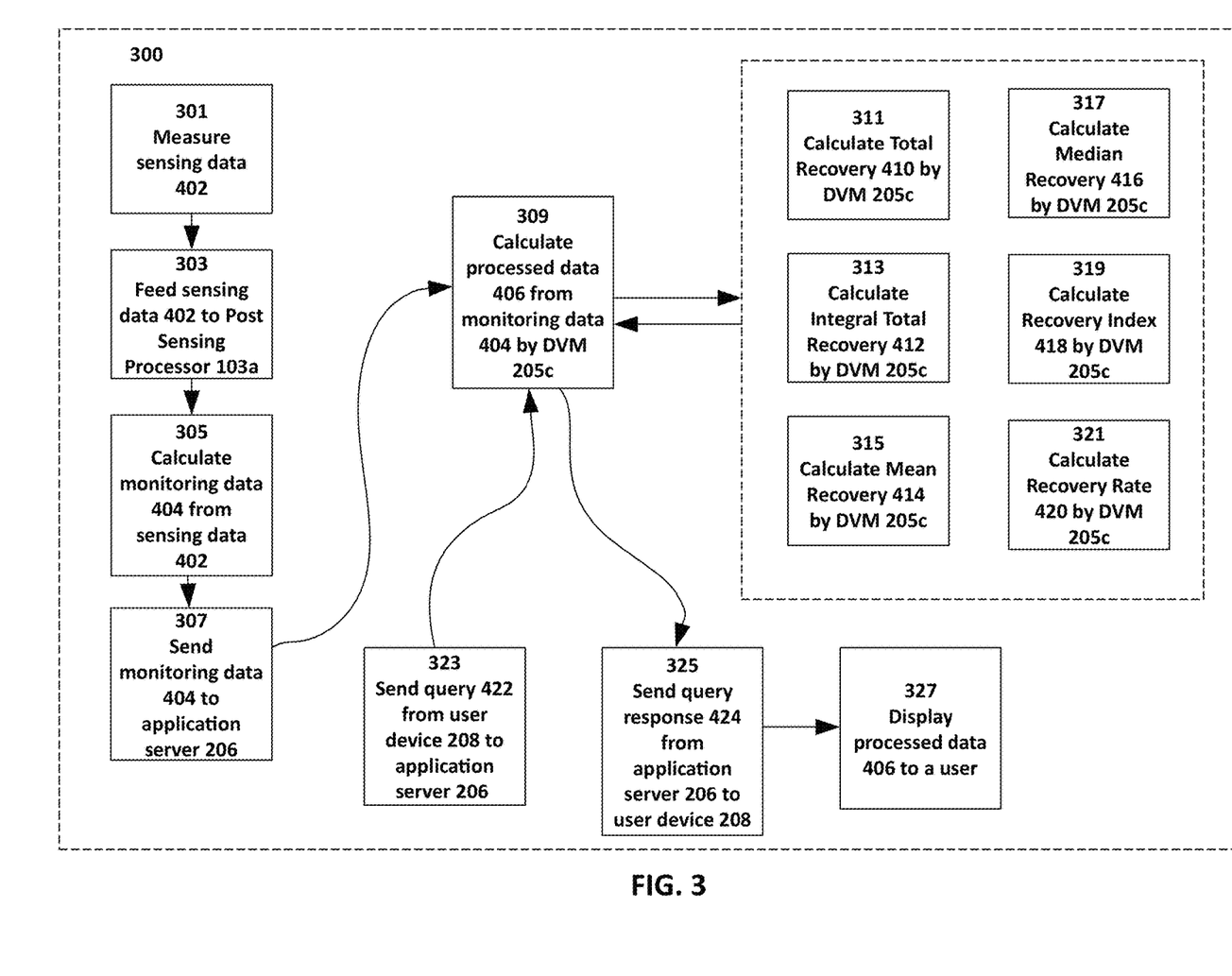
FIG. 3 is a flowchart of a heart-rate monitoring method in accordance with one or more embodiments of the present invention.

FIG. 3 is a flowchart of a heart-rate monitoring method in accordance with one or more embodiments of the present invention.

Figure 4:
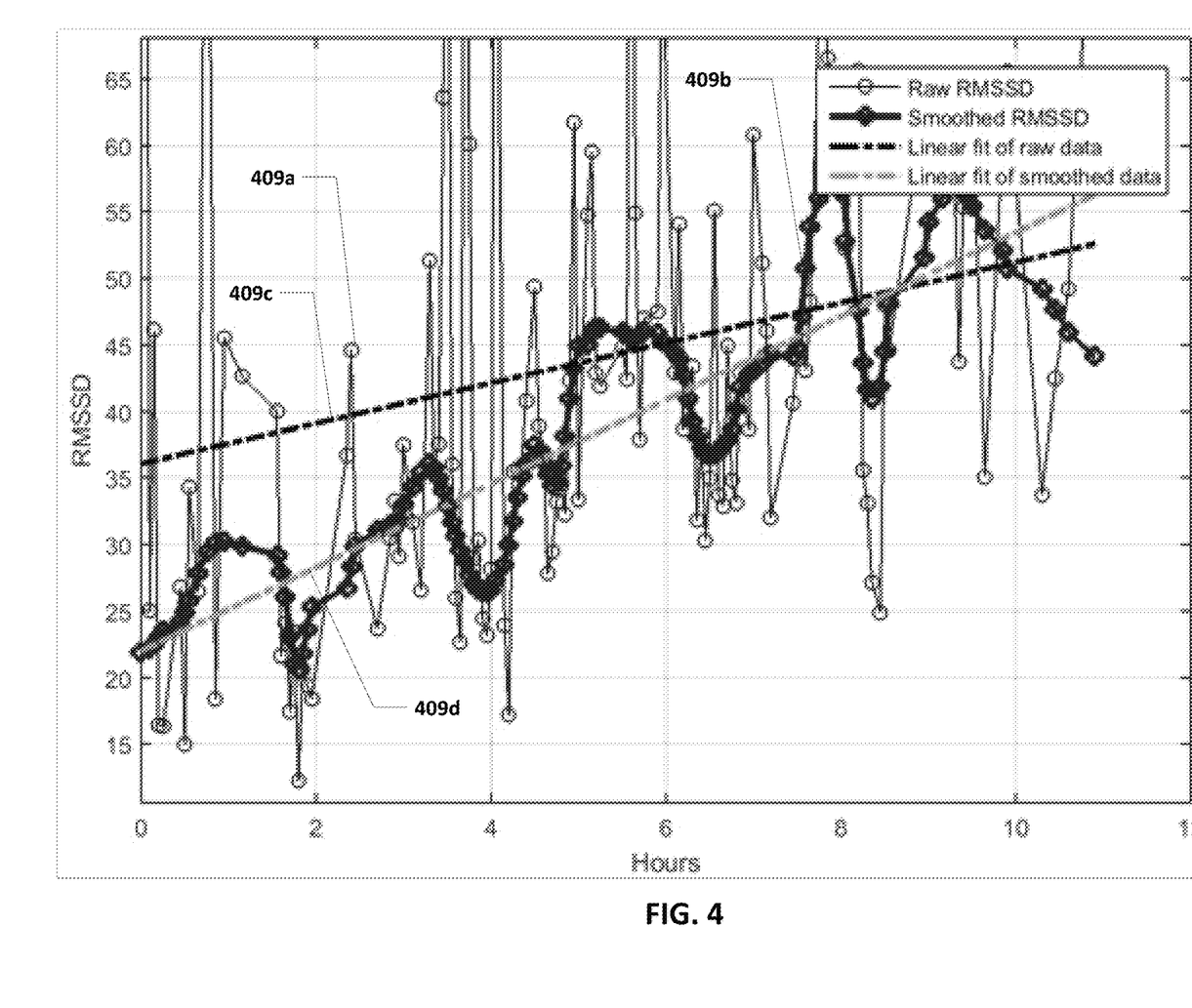
FIG. 4 is a graph illustrating an example of the heart-rate monitoring processed data in accordance with one or more embodiments of the present invention.

FIG. 4 is a graph illustrating an example of the heart-rate monitoring results in accordance with one or more embodiments of the present invention.

In accordance with one or more embodiments of the present invention, a contactless heart-rate monitoring device 100 detects signals associated with the beating heart of a monitoring subject over a period of time to determine one or more sensing data 402 and/or monitoring data 404 related to the heart rate variability (HRV) of the monitoring subject.

In accordance with one or more embodiments of the present invention, device 100 may be part of a contactless heart-rate monitoring system 200 that provides one or more data 402 and/or data 404 and/or one or more processed data 406 to one or more users.

In accordance with one or more embodiments of the present invention, a method of contactless heart-rate monitoring uses device 100 and/or system 200 to deliver to an authorized user one or more data related to HRV monitoring of a monitoring subject.

Advantageously, heart-rate monitoring device 100 and/or heart-rate monitoring system 200 overcome the drawbacks known in devices, i.e., skin irritation, inconvenience of use, cumbersome data-analytics, only limited data views such as "snapshot" or "few days" view, of the state-of-the-art approaches to measuring heart rate variability in order to increase a performance improvement efficiency, that is increase the speed, degree, and way by which the monitoring subject improves his/her performance.

Therein, heart-rate monitoring device 100, heart-rate monitoring system 200 that preferably incorporates a device 100, and/or heart-rate monitoring method 300 that preferably uses device 100 and/or system 200 are contactless with respect to the monitoring subject, fully automatic, and user-accessible and understandable data provided in a readily processed format for the whole night, which is the most important period for the recovery of both body and mind. That is, the heart-rate monitoring device 100, heart-rate monitoring system 200 that preferably incorporates a device 100, and/or heart-rate monitoring method 300 that preferably uses device 100 and/or system 200 advantageously eliminates the need for a monitoring subject to wear irritating ECG electrodes, chest band, wrist device, or any other wearable. In other words, physical contact between the heart-rate monitoring device 100 and the monitoring subject are eliminated. This makes it possible to monitor the HRV of vulnerable persons such as the elderly, children, medical patients, and/or mental patients who may not have the mental or physical ability to wear a monitoring device that requires physical contact. Moreover, heart-rate monitoring device 100, heart-rate monitoring system 200 that preferably incorporates a device 100, and/or heart-rate monitoring method 300 that preferably uses device 100 and/or system 200 makes it possible to monitor the HRV of prisoners or other persons who may not consent or be trusted to wear a monitoring device that requires physical contact.

Additionally, heart-rate monitoring device 100, heart-rate monitoring system 200 that preferably incorporates a device 100, and/or heart-rate monitoring method 300 that preferably uses device 100 and/or system 200 avoid cumbersome data export and/or third party analysis. Advantageously, after an initial set-up, it is not necessary for a user of device 100 or system 200 to turn on or off device 100 or system 200, respectively. It is sufficient that the user goes normally in to bed, which triggers automatic data acquisition and analysis. This allows continuous tracking all year round, and for athletes both intraseason and interseason analysis. Device 100 and/or system 200 makes HRV data available to a user in intuitive format using any suitable computing device as computer, laptop, tablet, mobile phone, etc.

Heart-rate monitoring device 100 may be any suitable computing device capable of carrying out at least the functions of method 300 and preferably be incorporated in system 200. Therein, preferably, but not necessarily device 100, is an Emfit QS device available from Emfit Oy of Finland or Emfit Corp. of Austin, Texas.

Heart-rate monitoring device 100 acquires BBI data of a monitoring subject for a specified period of time. Once an initial set-up (discussed below) has been performed, preferably, at a location has been selected where the monitoring subject is most likely to spend his night, heart-rate monitoring device 100 will automatically monitor heart beat intervals, i.e., BBI, of the monitoring subject for the whole night in a non-contact manner.

In accordance with one or more embodiments of the present invention, heart-rate monitoring system 200 comprises, preferably heart-rate monitoring device 100 (as described in one or more embodiments of the present invention), one or more communications networks 202 having one or more network interfaces 204, an application server 206, and a user device 208.

In accordance with one or more embodiments of the present invention, heart-rate monitoring device 100 comprises an electronics module 102, one or more communications devices 104, and a sensor 106. Heart-rate monitoring device is operably connected to a power source 108.

Electronics module 102 may be any suitable computing device that receives sensing data 402 from sensor 106. The electronics module is preferably disposed in a housing 101 may comprise a plurality of processing units, for example, unit 103a. Module 102 comprises a post-sensing data processor 103a that processes the sensing data 402 into monitoring data 404 and may store it for a predetermined time or permanently on a non-transitory computer-readable memory or media 103b.

Electronics module 102 further comprises a communicator 103c that uses communications device 104 to communicate with one or more other components of system 200 in accordance with method 300. Communications device 104 may be, but not necessarily, integrated in electronics module 102 and be a wireless Wi-Fi, Bluetooth, or other communications transceiver.

Sensor 106 preferably comprises a thin and slim form such as a sensor strip and is suitably sensitive enough so that it can be operably installed under, for example, a bed mattress 107 in a non-contact fashion with the monitoring subject. Sensor 106 is preferably in operable connection with electronics module 102 by a connection 110, which may be a hardwired connection as illustrated or a wireless connection.

Thus, an initial set-up of heart-rate monitoring device 100 requires that a location suitable for a pre-determined time of monitoring is chosen and relevant to that a suitable sensor location is determined. That monitoring location typically is a bed and the sensor location typically is under the mattress, i.e., the mattress overlays the bedspring or the bed splats, and is proximal to the heart of the monitoring subject when in the monitoring location. Device 100 during initial set-up is also preferably placed in communication via communicator 103c and communication device 104 with communications network 202 of system 200. That typically means that device 100 is made operably connected to a Wi-Fi router on communications network 202 for two-way communication with network 202.

Sensor 106 is preferably made of dynamic vibration sensitive ferroelectret film and, in a step 301, senses, i.e., measures, sensing data 402, for example, in the form of a ballistocardiogram (BCG), of the heart of the monitoring subject. In a step 303, sensor 106 feeds via connection 107 the sensing data to post-sensing processor 103a. In a step 305, processor 103a extracts, calculates, the heart beat intervals (BBI) as monitoring data 404 using Emfit Ltd in-house technology from the sensing data 402, which, for example, was in the form of BCG signal.

In accordance with one or more embodiments of the present invention, sensor 106 can also provide sensing data 402 to electronic module 102 as pressure and/or vibration sensitive data, such as PVDF (as, for example, used by Beddit), PZT (as, for example, used by EarlyeSense), or force sensing resistor (FSR) data. Thus, in accordance with one or more embodiments of the present invention, sensor 106 may comprise an optical cable, an air pressure sensor in an air-mattress (as, for example, used by BamLabs), or radar emission/reflection (as, for example, used by ResMed+). In accordance with one or more embodiments of the present invention, sensor 106 may also comprise optical led technology such as that known for use in pulse oximeters to obtain sensing data 402. Similarly, sensor 106 may also comprise ECG principles that in whole or in part obtain sensing data 402.

In a step 307, communicator 104 uses network interface 204 and/or network 202 to send monitoring data 404 to application server 206. Application server 206 may be any computing device suitable for performing its functions in method 300. Preferably, application server 206 comprises a communications device 205a, non-transitory computer-readable memory and/or media 205b, a data processing and visualization module ("DVM") 205c, and an application programming interface (API) that is user-accessible from user device 208. Communications device 205a receives monitoring data 404.

DVM 205c is the core of the analysis of heart beat intervals and enables the user to monitor his/her physical and mental (work, training, etc) load in the evening, recovery during the night, and final recovery status in the morning. Therein, DVM 205c computes meaningful measures for recovery status in the beginning, during, and at the end of the night, using varying length of time to define "beginning", "during", and "end" of the night, as well as different methods to model the data.

Therein, in a step 309, DVM 205c calculates one or more processed data 406 from monitoring data 404. Processed data 406 preferably comprises HRV index values for the whole night in short windows, which may include, but not be limited to, for example to RMSSD, and HRV index short values having a time length from 1 to 5 minutes.

In accordance with one embodiment of the present invention, processed data 406 preferably comprises smoothing short term measurements that allow one or more clearer more-understandable user-accessible graphs, and computing recovery index as, for example, but not limited to, a simple linear regression to smoothed data, or by comparing statistical value (including, but not limited to mean, median, minimum, maximum) of the HRV index within certain window (e.g. one hour) in the beginning of the night to similar window in the end of the night, and computing the ratio between these two.

In accordance with one embodiment of the present invention, the information above is best illustrated using FIG. 4, wherein the HRV index 408 is chosen to be RMSSD in this case. Thin circles 409a depict individual raw RMSSD values computed within each 3 minute window through the whole night. Thicker circles 409b are acquired by smoothing (using, for example, but not limited to, moving average) the raw RMSSD data to get a clearer picture. The dashed line 409c is linear regression of raw RMSSD data, and green dashed line 409d is linear regression of smoothed RMSSD data.

In a step 311, DVM 205c calculates a "Total Recovery" 410, which is a number indicating how much evening and morning values have changed. DVM 205c may calculate this in step 311 in one of two ways: (1) for example, based on, but not limited to, linear regression (fitted to smoothed data) as difference of regression line start and end y-coordinate, or by (2) comparing statistical value of said HRV index (including, but not limited to mean, median, minimum, maximum) within certain window (e.g. one hour) in the beginning of the night to similar window in the end of the night, and computing the difference between these two. In the example of FIG. 4, Total Recovery 410 is based on linear regression and has 34.3 RMSSD units.

In a step 313, DVM 205c calculates "Integral Total Recovery" 412 which is a number indicating the area under the chosen HRV index graph. DVM 205c assumed that, for example in the case of RMSSD, higher value indicates better recovery. It is worth noting, that this differs from Total Recovery in the sense that Total Recovery does not take into account anything that happens between evening and morning value, whereas Integral Total Recovery 412 is a measure for the whole night.

In a step 315, DVM 205c calculates "Mean Recovery" 414, which is simply a mean of all nightly values of the chosen HRV index.

In a step 317, DVM 205c calculates "Median Recovery" 416, which is simply a median of all nightly values of the chosen HRV index.

In a step 319, DVM 205c calculates "Recovery Index" 418, which is a number indicating amount of change (ratio) in measured HRV index (e.g. RMSSD) between evening and morning reading, and it can be based, but not limited to, either on linear regression start and end values, or by comparing statistical value (including, but not limited to mean, median, minimum, maximum) within certain window (e.g. one hour) in the beginning of the night to similar window in the end of the night, and computing the ratio between these two. In the example of FIG. 4, Recovery Ratio based on average of first and last 90 minute sequence is 1.98 with start RMSSD of 26.0 and end RMSSD of 51.7.

In a step 321, DVM 205c calculates "Recovery Rate" 420, which can be computed by bringing the recovery time in to the equation, resulting speed of change per unit of time. Once again, computation can be based, but not limited to, either on linear or more complex regression, or comparison of start and end segments of given length. In the case of FIG. 1, Recovery Rate based on linear regression is 3.1 RMSSD units/hour. This corresponds to steepness of linear fit of smoothed data.

Thus, herein, processed data 406 comprises data 410, 412 414, 416, 418, and 420 and, in a step 323, the application server response to a query 422 form the user utilizing user device 208 provides processed data 406. For example, a user can send a query 420 for a Recovery Index 418. In response, step 319 is performed by DVM 205c and, in a step 325, application server 206 provides processed data 406 as a query reply 424 to the user on user device 208 via network 202.

Advantageously, in a step 327, user device 208 will display processed data 406 to a user who will be able to immediately interpret the data. For example, Recovery Index values near 0 indicate that no significant recovery has occurred, whereas clearly positive values indicate recovery, and clearly negative values deterioration.

Obviously, if there is no load (due to stress, training, etc.), there is no need for recovery, and values around 0 are acceptable. To identify this situation, a user can use system 200 and/or method 300 to obtain evening values and compare these to long term evening values at least in two different settings, (1) in the case where significant recovery has occurred, and 2) in the case where significant recovery has not occurred. If evening values are close to case 1, the user will be able to use system 200 and/or method 300 to determine when the user could expect to see some significant recovery, and if this is not the case, it is a sign of some malfunction to be addressed.

Figure 5:
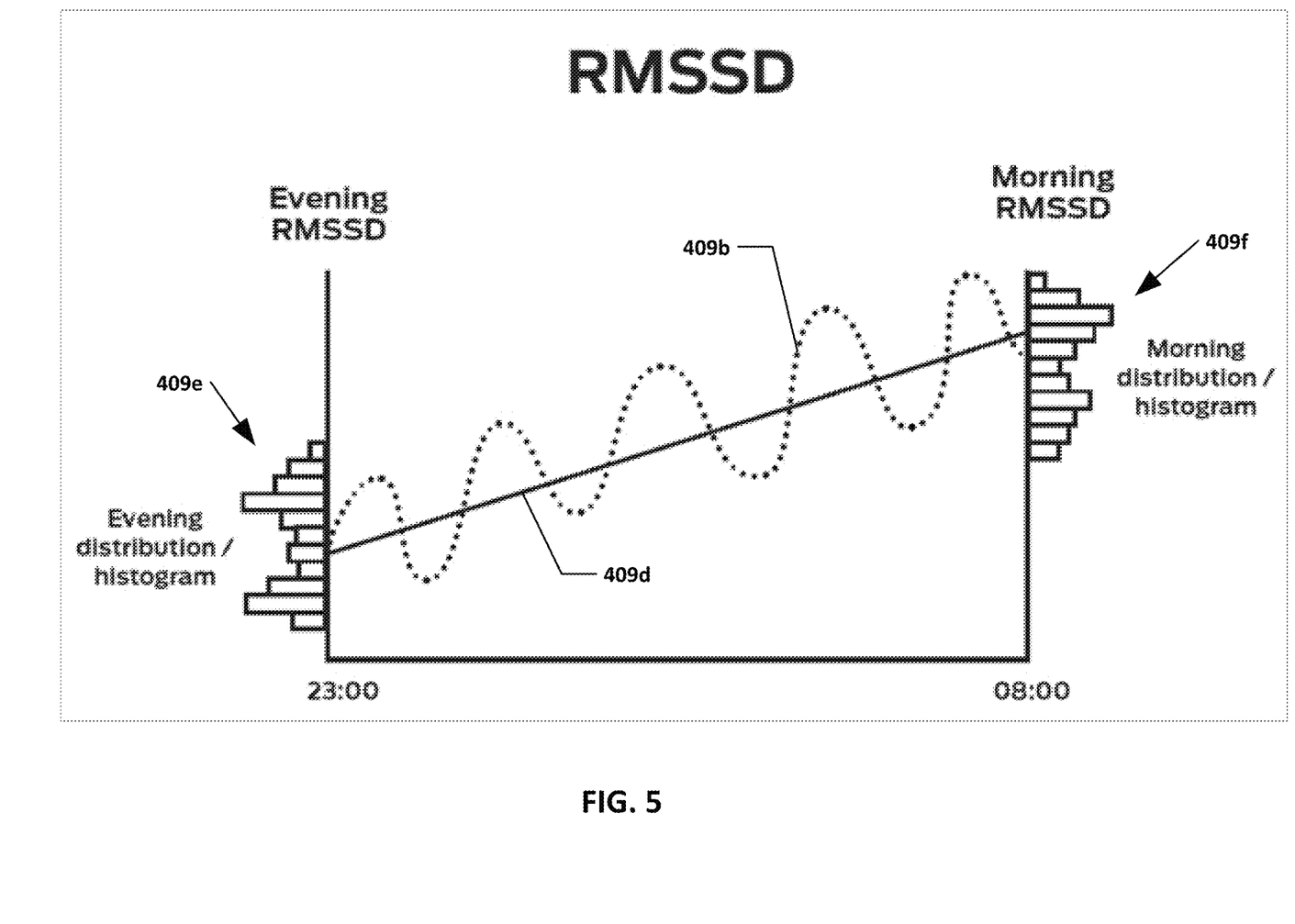
FIG. 5 is a graph illustrating an example of the heart-rate monitoring processed data showing a user-accessible graph with histograms in accordance with one or more embodiments of the present invention.

Herein, method 300 provides the ability to determine, display, and analyze baseline or historical values of user-accessible meaningful HRV indices, namely, but not limited to, evening and morning RMSSD. In accordance with one or more embodiments of the present invention, method 300 calculates statistical distribution of earlier values of the said variable, and display at least range (i.e. minimum or maximum) of this distribution, or preferably an informative graphic, for example, but not limited to, as a vertically tilted histogram or probability density function on the sides of the whole night RMSSD graph. In FIG. 5, a whole night RMSSD graphic is displayed, augmented with vertically tilted distribution of evening RMSSD values as a histogram at the left hand side, and similarly, distribution of morning RMSSD values at the right hand side.

Therein, user device 208 can display graphical representations of the historical behavior of the particular variable the user can intuitively see how current values relate to cumulative historical data, and also detect modes discussed earlier. As seen in FIG. 5, circles 409b are acquired by smoothing (using, for example, but not limited to, moving average) the raw RMSSD data to get a clearer picture. Line 409d is linear regression of smoothed RMSSD data. Histogram 409e of evening RMSSD has two peaks, one lower peak corresponding to heavy days, and higher to lighter ones. Advantageously, it is easy for the user to assess whether training load has been sufficient or not in the "heavy" training day, or if the "light" training day really has been light, or if there has been uncontrollable stress during the day that should have been "light". Similarly, with morning RMSSD values the user can see if he/she is fully recovered with morning RMSSD value near or above the upper histogram peak of histogram 409f, or if the recovery is still in progress or there is some physiologic or mental malfunction, and morning RMSSD value is near or below the lower histogram peak.

On the other hand, the athlete can monitor the training load by considering evening values. Sufficiently heavy training session should produce significant drop in the evening value, and this should be followed by nocturnal recovery. Therein, the performance improvement efficiency has been increased.

In an alternative, application server 206 is integrated in user device 208 and all steps and functions disclosed herein with respect to application server 206 or its components are, thus, performed by user device 208.

While the invention has been described in conjunction with specific embodiments, it is to be understood that many alternatives, modifications, and variations will be apparent to those skilled in the art in light of the foregoing description.

What is claimed is:

1. A heart rate monitoring system for monitoring heart rate variability of a monitoring subject; the heart rate monitoring system comprising:
a contactless heart rate monitoring device adapted to not being in physical contact with the monitoring subject during a monitoring period, the heart rate monitoring device comprising
a sensor providing sensing data of the monitoring subject during the monitoring period;
a post-sensing data processor for processing the sensing data into monitoring data; and
a communications device for communicating with the contactless heart rate monitoring device and an application server;
the application server for processing the monitoring data into processed data describing the monitoring heart rate variability of the monitoring subject; and
an user device for issuing a query and displaying the processed data,
wherein the sensor comprises a dynamic vibration sensitive ferroelectric film.

2. The heart rate monitoring system of claim 1, wherein post-sensing data processor processes the sensing data in a form of a ballistocardiogram (BCG) of the heart of the monitoring subject during the monitoring period.

3. The heart rate monitoring system of claim 1, wherein the sensing data is selected from pressure or vibration sensitive data, air pressure sensor data, or pulse oximetry data.

4. The heart rate monitoring system of claim 1, wherein the monitoring data comprises time measurements between heart beats of the monitoring subject.

5. The heart rate monitoring system of claim 1, wherein the sensor has a thin and slim strip form.

6. The heart rate monitoring system of claim 1, further comprising a network for communicating among the user device and application server.

7. The heart rate monitoring system of claim 1, wherein the user device comprises a data storage for storing the sensing data.

8. The heart rate monitoring system of claim 1, wherein the user device comprises a data storage for storing the monitoring data.

9. The heart rate monitoring system of claim 1, wherein the sensor monitors continuously during the monitoring period.

10. A heart rate monitoring system for monitoring heart rate variability of a monitoring subject; the heart rate monitoring system comprising:
a contactless heart rate monitoring device adapted to not being in physical contact with the monitoring subject during a monitoring period, the heart rate monitoring device comprising
a sensor providing sensing data of the monitoring subject during the monitoring period;
a post-sensing data processor for processing the sensing data into monitoring data; and
a communications device for communicating with the contactless heart rate monitoring device and an application server;
the application server for processing the monitoring data into processed data describing the monitoring heart rate variability of the monitoring subject; and
an user device for issuing a query and displaying the processed data, wherein the sensor consists of a dynamic vibration sensitive ferroelectret film.

11. The heart rate monitoring system of claim 10, wherein post-sensing data processor processes the sensing data in a form of a ballistocardiogram (BCG) of the heart of the monitoring subject during the monitoring period.

12. The heart rate monitoring system of claim 10, wherein the sensor monitors continuously during the monitoring period.

13. The heart rate monitoring system of claim 10, wherein post-sensing data processor processes the sensing data in a form of a ballistocardiogram (BCG) of the heart of the monitoring subject during the monitoring period.

* * * * *